(12) United States Patent
Middlesworth et al.

(10) Patent No.: US 7,351,297 B2
(45) Date of Patent: Apr. 1, 2008

(54) COMPOSITE ELASTIC WEB

(75) Inventors: Jeffrey Alan Middlesworth, Wauconda, IL (US); Tze Wan Pansy Chung, Fox River Grove, IL (US); Stephen D. Bruce, Crystal Lake, IL (US); Andrew James Peacock, Terre Haute, IN (US)

(73) Assignee: Tredegar Film Products Corp., Richmond, VA (US)

( * ) Notice: Subject to any disclaimer, the term of this patent is extended or adjusted under 35 U.S.C. 154(b) by 346 days.

(21) Appl. No.: 10/945,104

(22) Filed: Sep. 21, 2004

(65) Prior Publication Data

US 2006/0062963 A1  Mar. 23, 2006

(51) Int. Cl.
  *B32B 37/00* (2006.01)
(52) U.S. Cl. .................. 156/73.1; 156/161; 156/164; 156/229
(58) Field of Classification Search ............ 156/73.1, 156/161, 163, 164, 229, 308.2, 308.4
See application file for complete search history.

(56) References Cited

U.S. PATENT DOCUMENTS

| | | | |
|---|---|---|---|
| 3,054,148 A | 9/1962 | Zimmerli | 18/56 |
| 4,041,203 A | 8/1977 | Brock et al. | 428/157 |
| 4,155,693 A | 5/1979 | Raley | 425/363 |
| 4,223,059 A | 9/1980 | Schwarz | 428/198 |
| 4,252,516 A | 2/1981 | Raley et al. | 425/290 |
| 4,374,888 A | 2/1983 | Bornslaeger | 428/198 |
| 4,404,052 A | 9/1983 | Persson et al. | 156/73.1 |
| 4,508,256 A | 4/1985 | Radel et al. | 228/152 |
| 4,509,908 A | 4/1985 | Mullane, Jr. | 425/290 |
| 4,720,415 A * | 1/1988 | Vander Wielen et al. | 428/152 |
| 4,995,930 A | 2/1991 | Merz et al. | 156/209 |
| 5,143,679 A | 9/1992 | Weber et al. | 264/288.8 |
| 5,382,461 A | 1/1995 | Wu | 428/86 |
| 5,442,172 A | 8/1995 | Chiang et al. | 250/237 |
| 5,591,278 A | 1/1997 | Marcu | 152/152.1 |
| 5,591,510 A | 1/1997 | Junker et al. | 428/132 |
| 5,628,741 A | 5/1997 | Buell et al. | 604/385.2 |
| 5,635,275 A | 6/1997 | Biagioli et al. | 428/132 |
| 5,635,276 A | 6/1997 | Biagioli et al. | 428/132 |
| 5,660,882 A | 8/1997 | McBride et al. | 427/294 |
| 5,680,653 A | 10/1997 | Mathis et al. | 2/123 |
| 5,698,054 A | 12/1997 | Biagioli et al. | 156/145 |
| 5,733,628 A | 3/1998 | Pelkie | 428/138 |
| 5,762,643 A | 6/1998 | Ray et al. | 604/383 |
| 5,783,014 A | 7/1998 | Biagioli et al. | 156/209 |
| 5,382,461 A | 11/1998 | Wu | 428/86 |
| 5,861,074 A | 1/1999 | Wu | 156/209 |
| 6,242,047 B1 | 6/2001 | Johnson et al. | 427/361 |
| 6,303,208 B1 | 10/2001 | Pelkie | 428/138 |

(Continued)

FOREIGN PATENT DOCUMENTS

DE   198 26 455 A1   9/1999   .............. 27/12

*Primary Examiner*—James Sells
(74) *Attorney, Agent, or Firm*—Troutman Sanders; Bernard G. Pike; Joseph A. Tessari (57) ABSTRACT

A method for producing a composite web includes supplying two or more webs to an activation mechanism, where the webs are in an unbonded state relative to each other. The method further entails simultaneously activating the webs while they are in a face to face relationship and in an unbonded state, and then bonding the webs to form a composite web.

8 Claims, 3 Drawing Sheets

U.S. PATENT DOCUMENTS 6,383,431 B1   5/2002   Dobrin et al. .............. 264/154
6,491,776 B2  12/2002   Alper et al. ................ 156/161
7,037,569 B2   5/2006   Curro et al. ................ 428/138

* cited by examiner

COMPOSITE ELASTIC WEB

FIELD OF THE INVENTION

The embodiments relate to webs, and to processes for activating and thereby rendering soft to the touch, webs of films or fibrous materials, or laminates of films and fibrous materials, such as would be encountered in certain products, such as diapers, articles for the control of the effects of incontinence, other hygiene articles, and bandages. Embodiments also relate to the composite webs made thereby, and to articles manufactured from those webs.

DESCRIPTION OF RELATED ART

Absorbent articles such as diapers, training pants or incontinence garments are required to provide a close, comfortable fit about the wearer and contain body exudates while maintaining skin health. It therefore is desirable that elastic materials for use in absorbent articles be soft to the touch. Softness can be achieved by laminating the elastic material to a soft and generally fibrous material, such as a nonwoven fabric to thereby form a soft web.

It has been found that a process of "activating" a web by stretching it in one or more directions induces softness into the web as perceived by a person touching it. A method for stretching fiber or film webs in either the machine direction or the cross direction of the web, or both, is described in U.S. Pat. Nos. 4,223,059; 5,861,074; 5,422,172; and 5,382,461; the disclosures of each of which are incorporated by reference herein in their entireties.

Activation as exemplified in these documents refers to the process of stretching the composite web beyond the total extensibility of the film or nonwoven web or webs that make up the material. In the case of nonwoven webs, breakages of inter fiber bonds can occur. The yielded material then feels soft to the touch. The activation generally is accomplished by one of two processes. One process involves stretching by a set of intermeshing gears, and the other process involves stretching between driven rolls (driven at different speeds) in the machine direction of the web.

U.S. Pat. No. 5,143,679 describes activation in two steps. This document discloses intermeshing gears that are used in which the depth of engagement in the second step is higher than that in the first step. Thus, the level of activation in the second step is higher than in the first step.

One of the disadvantages of activation, in particular as it is applied to laminates of film with nonwoven materials, or of nonwovens alone, is that the process disrupts the structure of the nonwoven. It therefore is necessary to use a high quality and therefore expensive precursor nonwoven in the activation process, in order to maintain a viable structure in the activated product. Typically basis weights of 20 grams per square meter (gsm) or greater are used commercially.

The description herein of disadvantages and problems with known processes, materials, and apparatus, is not intended to limit the scope of the invention to the exclusion of these known processes, materials, and apparatus. Indeed, certain embodiments of the invention may include one or more of the known processes, materials, and apparatus without suffering from the disadvantages or problems described herein.

SUMMARY OF THE EMBODIMENTS

In the embodiments, an activated, laminated web that comprises a less expensive, lower basis weight, precursor nonwoven is provided, wherein the activation is carried out before the component webs in the laminate have been bonded. After activation, the component webs are bonded in a face to face relationship by using the pressure generated by the activating process provided sufficient heat is applied to the interface between the webs. Tensile and elongational properties in the finished product preferably are superior to more expensive nonwovens that undergo activation while bonded to a second web.

During the activation process, the component webs are believed to be capable of movement relative to each other in the plane of the web. While not intending on being bound by any theory of operation, it is believed that this feature results in the superior tensile and elongation values that are obtained from laminated precursor webs activated and then bonded by this method.

In the embodiments, combined activation and thermal bonding can be performed on conventional intermeshing gear activation equipment, equipped with heated activation rolls. A nonwoven fabric and an apertured bi- or tri-laminate elastomer film can be contacted to one another just prior to the activation rolls. As the two layers enter the nip they are activated simultaneously, but independently. At the closest point of approach the tooth tips on one roll would be a few thousandths of an inch away from the bottom of the opposing groove. It is here that thermal bonding can take place, embedding the nonwoven fabric into the softened elastomer film. The thermal bonds take the form of continuous lines corresponding to the tops of the teeth on the activation rolls. The resulting activated material then may be slit and wound up in the conventional manner.

In a further embodiment, it is possible to simultaneously combine two layers of nonwoven fabric with an apertured elastic film to produce a laminate structure or an apertured elastic film with a single layer of nonwoven fabric to produce a bi-laminate.

Another embodiment includes a laminated material comprised of at least one nonwoven fabric and an elastomer film made by the process described herein. The laminated material has improved tensile and elongation properties.

BRIEF DESCRIPTION OF THE FIGURES

The invention can be best understood by reference to the figures, which are summarized here.

DETAILED DESCRIPTION OF THE EMBODIMENTS

The terminology used herein is for the purpose of describing particular embodiments only, and is not intended to limit the scope of the claims. As used throughout this disclosure, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the embodiments, the preferred methods, devices, and materials are now described. All publications mentioned herein are cited for the purpose of describing and disclosing the various webs, films, laminates, processing methods and articles that are reported in the publications and that might be used in connection herewith. Nothing herein is to be construed as an admission that such disclosures are prior art.

Throughout this description, the term "web" refers to a material capable of being wound into a roll. Webs can be film webs, nonwoven webs, laminate webs, apertured laminate webs etc. The face of a web refers to one of its two dimensional surfaces, as opposed to its edge. The term "composite web" refers to a web that comprises two or more separate webs that are bonded in a face to face relationship. The bonding can be through the edges of the component webs, although the component webs lie in a face to face relationship with each other. Webs are described herein to be in an "unbonded state" relative to each other when the webs are in surface to surface contact with each other but there are no bonds securing one web to the other.

The term "film" in this description refers to a web made by extruding a molten sheet of thermoplastic polymeric material by a cast or blown extrusion process and then cooling said sheet to form a solid polymeric web. Films can be monolayer films, coextruded films, coated films, and composite films. Coated films preferably are films comprising a monolayer or coextruded film that are subsequently coated (for example, extrusion coated, impression coated, printed, or the like) with a thin layer of the same or different material to which it is bonded. Preferably, the coating is incapable of separation after bonding. Composite films preferably are films comprising more than one film where the at least two films are combined in a bonding process. Bonding processes may incorporate adhesive layers between the film layers.

Throughout this description, the expression "apertured films" denotes films in which there exist a plurality of holes that extend from one surface to a second surface. A two dimensional apertured film is a film in which no three dimensional structure exists in the holes, which then connect the second surface of a flat film to the first surface of the film. A three dimensional film is a film with protuberances, and a three dimensional apertured film is a film in which a three dimensional structure exists in the apertures (e.g., the apertures have a depth that is thicker than the thickness of the film).

The term "nonwoven" means a web comprising a multitude of fibers. The fibers can be bonded to each other or can be unbonded. The fibers can be staple fibers or continuous fibers. The fibers can comprise a single material or can comprise a multitude of materials, either as a combination of different fibers or as a combination of similar fibers each comprised of different materials.

As used herein "nonwoven fibrous web" is used in its generic sense to define a generally planar structure that is relatively flat, flexible and porous, and includes staple fibers or continuous filaments. For a detailed description of non- wovens, see "Nonwoven Fabric Primer and Reference Sampler" by E. A. Vaughn, Association of the Nonwoven Fabrics Industry, 3d Edition (1992).

The nonwoven web can be the product of any process for forming the same, such as nonwoven spunbond and melt blown nonwoven webs. The nonwoven web can include a composite or combination of webs. In one embodiment, the web is a spunbond material, made of polypropylene fiber. The nonwoven web can, however, comprise any polymeric material from which a fiber can be produced. For example, the nonwoven web may comprise fibers of polyethylene, polypropylene, elastomers, polyesters, rayon, cellulose, nylon, and blends of such polymers fibers. Fibers that comprise different polymers also can be blended.

The term "extensibility" as used herein refers to the maximum amount of strain (in %, relative to the zero strain state) that can be applied to a web in a given direction by a tensile force without breakage of fibers, or bonds between fibers. For a nonwoven web to be extensible in any given direction means that when a tensile force is applied to the web in that direction, the web expands in that direction, and a strain is induced in the web, substantially without breakage of fibers, or of bonds between fibers.

The term "screen" as used herein refers to a three-dimensional molding apparatus comprising indentations used to form protuberances or apertures in films. In a particular embodiment, screens comprise tubular members, having a width and a diameter. In alternative embodiments screens comprise belts having a width and a length. The transverse direction is the direction parallel to the width of the screen. The machine direction is the direction parallel to the direction of rotation of the screen, and is perpendicular to the transverse direction.

The term "perforation" as used herein refers to an aperture in the screen. The term "protuberance" as used herein refers to a three-dimensional member comprising an apertured base portion located in the plane of the first surface of the film and a sidewall portion extending generally in the direction of the second surface of the film. Each base portion has a sidewall portion. Sidewall portions terminate in "ends" located in the plane of the second surface of the film. The ends of the protuberances may be apertured or unapertured. The apertures in the base portions of the protuberances, also called "primary apertures," preferably are in the shape of polygons, for example squares, hexagons, pentagons, ellipses, circles, ovals, or slots, in a regulated or random pattern. The protubered ends, if apertured, are called "secondary apertures," and are preferably in the shape of polygons, e.g., squares, hexagons, pentagons, ellipses, circles, ovals, or slots.

As used herein, the expression "absorbent articles" denotes articles that absorb and contain body fluids and other body exudates. More specifically, an absorbent article includes garments that are placed against or in proximity to the body of a wearer to absorb and contain the various exudates discharged from a body. As used herein the term "elastic" is used to describe a material which upon application of a tensile force is extensible to a stretched length preferably at least 2× its initial, unstretched length, and that will retract to at most 1.75× of its initial, unstretched length upon release of the elongating force.

Any film can be used in the embodiments. The starting materials for the film preferably are mixed and heated in any suitable mixing and heating apparatus, such as extrusion apparatus. Extrusion processes are well known in the art, and any suitable extrusion process can be used to prepare the melt sheet of the film, using the guidelines provided herein.

These extrusion processes usually comprise mechanisms for feeding materials to the extruder, mechanisms for melting and mixing materials, mechanisms for transporting the molten materials to a forming die, and mechanisms for cooling the molten sheet of polymer to form a polymer film. In case a second film or web is laminated to the molten sheet, such second film or web may participate in the cooling process.

Methods and apparatus suitable for feeding the raw materials to the extruder generally are known. A preferred feeding mechanism comprises a conveying mechanism such as a vacuum pump connected to a vacuum pipe, the pipe being submerged in a reservoir of polymer material. In a controlled manner the pump generates vacuum in the pipe causing the pipe to suction polymer from the reservoir and to deposit it in a feed hopper. The feed hopper typically contains a metering device that deposits accurately controlled amounts of polymer into the extruder receiving cavity. Multiple cavities and feed hoppers may be present in a single extruder thereby enabling feeding of multiple components. In addition, antistatic and vibratory devices can be positioned at or near the feed hoppers to assist in accurately dosing the polymer. Other feeding mechanisms known to those skilled in the art or later discovered also are contemplated for use herein.

A preferred melt forming die is a cast die, but other types of dies are possible such as blown film dies. The die forms a molten polymer sheet that is subsequently cooled to create a film or a laminate structure.

In an alternative embodiment, molten polymer exits the extruder through a pelletizing die (a flat, cylindrical plate with multiple small openings). As the polymer passes through the die, it forms strings of polymer. The strings may be subsequently cooled and cut by a rotating knife, and the cut strings are called "compounded pellets." Compounded pellets then can be transported to a second extruder where they are melted again, transported to a die, and formed into a sheet that is subsequently cooled to form a film or laminate structure. In yet another alternative arrangement, the compounded pellets may be combined with other polymer pellets in the second extruder.

Cooling mechanisms also are well known in the art, and any cooling mechanism now known or later discovered can be used to cool the polymer exiting the extruder to form a film. A primary cooling mechanism can include an embossing station comprising two cooled rolls that are pressed against each other. The molten polymer is caused to pass between the embossing rolls (called engraving and anvil rolls, respectively) where it is cooled by contact with the cooler rolls. Alternatively, the rolls can both be smooth chill rolls without an engraving or embossing roll. Another well known cooling device comprises passing the polymer sheet over a single roll and applying an air or cool water curtain to the molten polymer to cause it to contact the single cooling roll. Both the air curtain and the contact with the roll contribute to cooling.

Another well known cooling mechanism comprises passing the polymer sheet over an apertured screen while in the presence of vacuum. Vacuum causes the polymer sheet to come into close contact with the screen causing the polymer to cool. In one embodiment the vacuum and screen combination cause the polymer sheet to conform to the shape of the apertured screen surface to form protrusions in the film. The side of the film that contacts the screen is called the formed film inner surface and the side of the film that is opposite the inner surface is called the formed film outer surface. The protrusions can be apertured, or they can be unapertured. Forming apertured polymer films in this manner is well known in the art, as exemplified by U.S. Pat. Nos. 3,054,148; 4,155,693; 4,252,516; 4,508,256; and 4,509,908; the disclosures of which are incorporated herein by reference in their entirety.

Other means of perforation include passing the film over a perforating roll from which pins or blades project, which enter the film and produce holes as the film passes over the roll. In these methods, a backing roll is generally used that holds the film in place against the perforating roll. The actual perforation then takes place in the nip between the perforating roll and the backing roll.

Intermeshing Gear (IMG) machine direction orientation typically is accomplished by stretching the film through a gear like pair of rollers. IMG activation can be carried out in the machine direction (MD) or in the transverse direction (TD) relative to the direction of motion of the web. In MD activation, a view of the cross section of the rolls looking down the axis of the rolls would show gear teeth cut into and around the circumference of the rolls, with their long axis substantially parallel with the roll axis. The teeth on one roll mesh into the grooves on the adjacent rolls in order to provide a stretching action to the web.

Rolls used for TD activation have fins and grooves positioned alternately along the axis of the roll and in the direction of travel of the web. The fins of one roll intermesh with the grooves of the adjacent roll, thereby providing points on adjacent fins against which the web is stretched in the transverse direction.

In both types of IMG activation, the shafts on which the rollers are mounted are positioned between two machine side plates, the first shaft preferably being located in fixed bearings and the second shaft preferably being located in bearings in slidable members. The position of the slidable members therefore is adjustable by use of wedge shaped elements operable by adjusting screws or other devices. Screwing the wedges out or in will move the vertically slidable member respectively down or up to further engage or disengage the gear-like teeth of the second intermeshing roll with the first intermeshing roll. Micrometers mounted to the side frames indicate the depth of engagement of the teeth of the intermeshing roll.

Air cylinders can be employed to hold the slidable members in their engaged position firmly against the adjusting wedges to oppose the force exerted by the material being stretched. These cylinders may also be retracted to disengage the upper and lower intermeshing rolls from each other for purposes of threading material through the intermeshing equipment or in conjunction with a safety circuit that would open all the machine nip points when activated.

A drive means typically is employed to drive the stationary intermeshing roll. If the second intermeshing roll is to be disengageable for purposes of machine threading or safety, it is preferable to use an antibacklash gearing arrangement between the second and first intermeshing rolls to assure that upon reengagement, the teeth of one intermeshing roll always fall between the teeth of the other intermeshing roll. This feature avoids potentially damaging physical contact between addendums of intermeshing teeth. If the intermeshing rolls are to remain in constant engagement, the second intermeshing roll typically need not be driven. Driving the second roll may be accomplished by the driven intermeshing roll through the material being stretched. The teeth are not designed to transmit rotational torque and do not contact metal-to-metal in normal intermeshing stretching operation.

An example of a particularly preferred embodiment is a stretching apparatus made by Northern Engraving and Machine, of Green Bay, Wis., which employs rollers with a tooth pitch preferably about 0.155", however a pitch of about 0.040" to 0.200" also is acceptable. The tooth depth preferably is 0.280", however, a tooth depth of about 0.030" to 0.500" also is acceptable. Tooth density at the roll circumference preferably is about one tooth per degree of angle subtended at the circumference of the roll. A particularly useful embodiment employs IMG rollers that can be temperature controlled from about 50° F. to about 210° F., and more preferably in a range of from about 70° F. to about 190° F., The roll temperature may be maintained through use of an internal flow of a heated or cooled liquid, an electrical system, an external source of cooling/heating, combinations thereof, and other temperature control and maintenance methods that will be apparent to those of ordinary skill in the art. A preferred embodiment for controlling the temperature of the rollers is internal flow of a heated or cooled liquid through the rollers. This allows either heating or cooling the rollers, depending on whether heating or cooling is desired.

The depth of engagement of the roller teeth determines the degree of elongation to which the web is subjected. A balance usually is drawn between the depth of engagement of the roller teeth and the precursor web composition, as these affect many important physical properties of the web. Some of the factors affecting the choice of pitch, teeth depth, and depth of engagement include the composition of the web, desired final properties (breathability, absorbency, strength, cloth-feel), and the width and diameter of the IMG rollers. The final application of the web also affects these choices because it determines desired final properties. The width of the IMG rollers presents economic and technical limitations—as the width increases, the weight of the rollers also increases, as does the amount of deflection experienced by the rollers. Deflection creates variation not only in the process of stretching, but also in the process of making the rollers, particularly as the pitch and tooth depth increases. Those skilled in the art are capable of varying the parameters of the rollers to achieve the desired stretching, using the guidelines provided herein.

Another embodiment of the invention involves incrementally stretching the webs of the invention without using IMG rollers. In this embodiment, the webs can be passed through the nip of a series of rollers rotating at different circumferential speeds. The rollers may include friction bearing surfaces to effect the incremental stretching. These rollers also may be heated or cooled to control the desired properties of the web.

The webs preferably include a nonwoven material and a film. Usually the film is made from a polymer, such as polyethylene, e.g., low density polyethylene (LDPE), linear low density polyethylene (LLDPE) or a mixture of LDPE and LLDPE, polypropylene, and combinations thereof. In one embodiment, the film is made from a mixture of at least about 10% by weight, or about 10% to about 50% by weight of MDPE (Medium Density Polyethylene), and the remainder LDPE, LLDPE or a blend of LDPE and LLDPE. The film also may be comprised of a mixture of at least 10% by weight, or about 10% to about 50% by weight of HDPE (High Density Polyethylene), and the remainder LDPE, LLDPE or a blend of LDPE and LLDPE. Each of the material formulations can include additional materials, usually in small percentages relative to the polymer. For example, the film may include processing aids, colorants (e.g. whiteners), and surfactants. The use of the term LLDPE here also includes those LLDPE's that are made using metallocene catalysts and are commonly referred to as mLLDPE.

The film also can be made from any suitable elastic material, such as natural or synthetic polymeric materials. Examples of suitable polymers include low crystallinity polyethylenes, metallocene catalyzed low crystallinity polyethylene, ethylene vinyl acetate copolymers (EVA), polyurethane, polyisoprene, butadiene-styrene copolymers, styrene block copolymers such as styrene/isoprene/styrene (SIS), styrene/butadiene/styrene (SBS), or styrene/ethylene-butadiene/styrene (SEBS) block copolymers. Blends of these polymers alone or with other modifying elastic or non-elastomeric materials also are contemplated as being useful. In certain embodiments, the elastomeric materials can comprise high performance elastomeric materials such as elastomeric block copolymers. An example of a suitable elastomeric block copolymer is sold under the brand name KRATON, a registered trademark of the Kraton Polymers of Houston, Tex.

The elastic film may include skin layers of, for example, a polyethylene blend, that are coextruded with the elastic layer to form a multilayered elastic material. The skin layers may include additives such as tackifiers, lower melting point polymers, and other components that may aid in the bonding process.

The nonwoven materials and the elastic materials are bonded to one another by a bonding means after, during, or simultaneously with the IMG stretching. Many means for bonding are available to one skilled in the art. Examples of means for bonding include, but are not limited to, thermal bonding, adhesive bonding, ultrasonic bonding, point bonding, vacuum lamination, mechanical bonding, solvent bonding and chemical bonding. Those skilled in the art are familiar with these known bonding means, and any or a combination of the bonding mechanisms can be used.

Thermal bonding includes the application of heat and pressure to two surfaces in order to bring about such physical changes as are necessary to cause the surfaces to adhere to the required degree. Such heat and pressure generally are applied using the nip between a pair of rolls. Thermal bonding also may include adhesive bonding, in which one or both of the surfaces has adhesive applied to it in the places where it is desired that bonding take place. Generally, the presence of an adhesive means that milder conditions of temperature and pressure are adequate to form a bond. In addition, the materials to be bonded may be coated or otherwise contacted with a pressure or temperature sensitive adhesive, where bonding is achieved upon application of the appropriate energy (heat or pressure).

Ultrasonic bonding typically entails a process performed, for example, by passing a material between a sonic horn and an anvil roll such as illustrated in U.S. Pat. Nos. 4,374,888 and 5,591,278, the disclosures of which are incorporated by reference herein in its entirety. In an exemplary method of ultrasonic bonding, the various layers that are to be bonded to one another may be simultaneously fed to the bonding nip of an ultrasonic unit. A variety of these units are available commercially. In general, these units produce high frequency vibration energy that melt thermoplastic components at the bond sites within the layers and join them together. Therefore, the amount of induced energy, speed by which the combined components pass through the nip, gap at the nip, as well as the number of bond sites determine the extent of adhesion between the various layers. Very high frequencies are obtainable, and frequencies in excess of 18,000 cps (cycles per second) usually are referred to as ultrasonic, however, depending on the desired adhesion between various layers and the choice of material, frequencies as low as 5,000 cps or even lower may produce an acceptable bond.

Point bonding typically includes bonding one or more materials together at a plurality of discrete points. For example, thermal point bonding generally involves passing one or more layers to be bonded between heated rolls that include, for example, an engraved pattern roll and a smooth calender roll. The engraved roll is patterned in such a manner that the entire fabric is not bonded over its entire surface, and the calender roll is usually smooth. As a result, various patterns for engraved rolls have been developed for functional as well as aesthetic reasons.

Adhesive lamination usually refers to any process that uses one or more adhesives that are applied to a web to achieve a bond between two webs. The adhesive can be applied to the web by means such as coating with a roll, spraying, or application via fibers. Examples of suitable adhesives are provided in U.S. Pat. No. 6,491,776, the disclosure of which is incorporated herein by reference in its entirety.

U.S. Pat. Nos. 4,995,930, 5,591,510, 5,635,275, 5,635,276, 5,660,882, 5,698,054, 5,762,643, 5,733,628, 5,783,014, 6,242,074, and 6,303,208 each describe a lamination technique called vacuum formed lamination (VFL), whereby a web substrate is laid upon a molten polymer sheet as successive portions of the sheet are passed over an apertured screen under the presence of vacuum. The disclosures of each of these patents are incorporated herein by reference in their entirety. The web substrate can be a nonwoven or it may be a thin polymeric substrate, breathable or non-breathable. The substrate may be a monolayer or multilayer substrate.

Mechanical bonding can be achieved by puncturing, or deforming, one web so that the layers are bonded mechanically, which means that they grip each other in some way using formations on the surface of each web. A hook and eye type of structure represents an example of a mechanical bond. Mechanical bonding can be accomplished with "spikes" on the IMG roll fins or teeth or, preferably, a ribbed or spiked pattern raised on the layon roll. This might be further assisted with corresponding grooves cut into the IMG roll fins or teeth.

Figure 1:
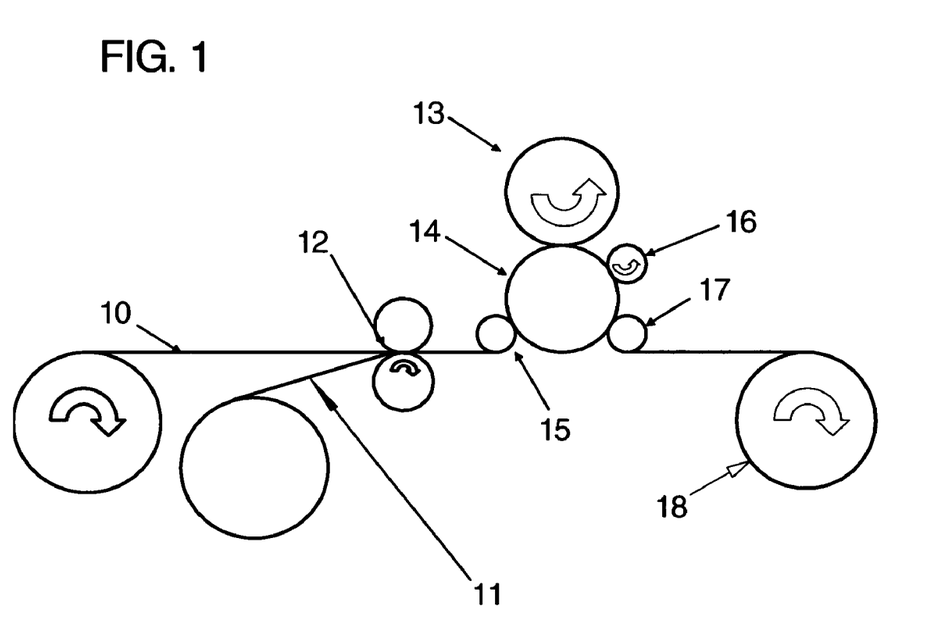
FIG. 1 is a schematic diagram of a process according to an embodiment, which shows two webs being fed simultaneously in an unbonded state to a pair of activation rolls, and then being bonded to each other by pressure applied to the web against one of the activation rolls.

Embodiments now will be explained with reference to the figures. FIG. 1 is a schematic diagram of an embodiment whereby a nonwoven (11) and a perforated film (10) stock are fed in a face to face relationship to a nip (12), and from there onto activation rolls (13 and 14) via a layon roll (15). FIG. 1 shows the nonwoven and perforated film being fed from rolls, although one skilled in the art will recognize that there are numerous ways of supplying webs in such a relationship to each other. Suitable nonwoven materials for use in the process include commercially available nonwovens, such as Sofspan 200 supplied by BBA Nonwovens of One Lakeview Place—Suite 204 Nashville, Tenn. 37214 USA. A suitable perforated film for use in the process include commercially available films, such as an elastomeric formed film supplied by Tredegar Film Products, Richmond, Va. under the trade name FLEXAIRE.

If desired, the activation rolls 13 and 14 can be heated or cooled by any suitable medium, including but not limited to electrical, steam, water, oil, or other heat transfer fluid. The webs preferably are activated in the nip between the activation rolls, and then bonded against one of the activation rolls (14) by pressure applied to the webs by a nip roll (16). The laminated and activated web then is removed from the activation roll (14) by a take off roll (17), and transported to a take up roll (18), although any suitable device for taking up the laminated, activated, web can be used in an embodiment of the invention. The advantage from an economic point of view of carrying out activation and bonding on one piece of equipment is readily apparent, and in the example will be given evidence that a superior product from the point of view of material properties will be given. Skilled artisans will appreciate, however, that embodiments of the invention encompass lamination downstream from activation rolls 13 and 14.

Figure 2:
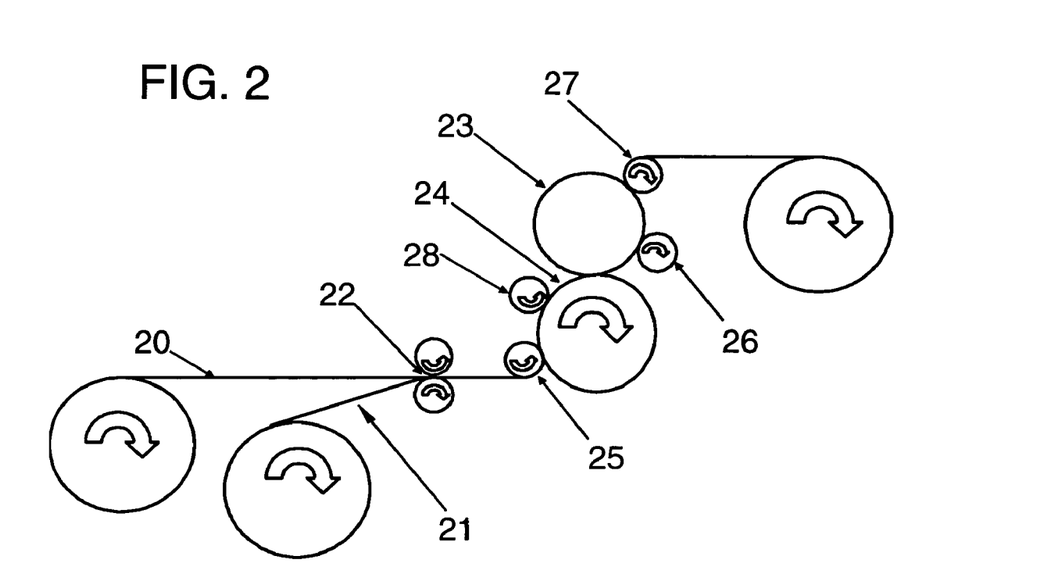
FIG. 2 is a schematic diagram of another process of an embodiment. In this process, two webs are fed simultaneously and in an unbonded state to a pair of activation rolls where they are prebonded against one of the activation rolls before activation. Activation then takes place on the same activation roll as the prebonding took place.

A further embodiment is illustrated in FIG. 2. Nonwoven (21) and perforated film (20) stock again are fed in a face to face relationship to a nip (22), and from there onto activation rolls (23 and 24) via a layon roll (25). In this embodiment, however, the webs are prebonded by a heated nip roll (28) that delivers the unbonded webs directly to the activation roll (24). This process has the advantage over other bonding and activation processes in that the bonding of the webs takes place at the teeth of the intermeshing gears, and the bonded web stays in register with the teeth through the activation process. The activation therefore takes place at unbonded regions of the web, where the original structure of the web has not been affected by the thermal bonding, and activation can be expected to be most efficacious.

A further nip (26) can be heated or cooled, as required by the product to be made, and can be used to provide a second bonding to the laminated, activated web. The relative degrees of bonding before and after activation then can be adjusted by choice of temperatures and pressures that are applied to the webs by nips 26 and 28. Roll 27 is a takeup roll that allows transfer of the laminated web from the activation roll 23 to a take up roll. The activation rolls (23 and 24) also can be heated or cooled as desired for best results.

Figure 3:
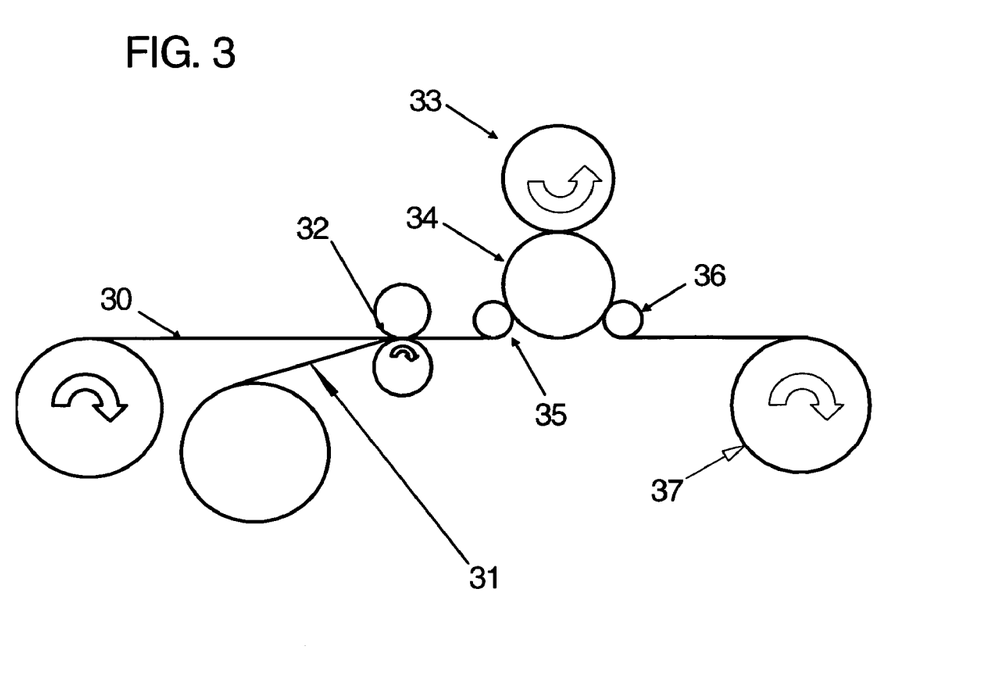
FIG. 3 is a schematic diagram of another process of an embodiment. In this embodiment, the webs are simultaneously fed to a pair of activation rolls in an unbonded state, and the pressure and heat applied during activation is used to bond the webs.

A further embodiment is shown in FIG. 3. In this embodiment, the bonding and activation take place simultaneously, while the webs are in between the teeth in the nip of the intermeshing gears on activation rolls 33 and 34. In this case, thermal energy from the activation rolls is sufficient to cause adhesion. Nonwoven (31) and perforated film (30) stock can be fed in a face to face relationship to a nip (32), and from there onto heated activation rolls (33 and 34) via a layon roll (35). In this embodiment, there is no nip roll to apply pressure to the activated web against the activation roll (34), as the bonding takes place simultaneously with activation while in the nip between rolls 33 and 34. In order to facilitate bonding in this way, adhesive can be applied to the film 30, and preferably a pressure sensitive adhesive is applied. A suitable adhesive is NS34-5647, commercially available from National Starch & Chemical Company, Bridgewater, N.J. A takeoff roll (36) then removes the bonded and activated web form the roll 34 and supplies the laminated web to take up roll 37.

EXAMPLE

Samples of nonwoven (Sofspan 200 supplied by BBA Nonwovens of One Lakeview Place—Suite 204 Nashville, Tenn. 37214 USA) and elastomeric formed film (elastomeric apertured film formed into a three dimensional shape via use of vacuum) were prepared as: (i) a bilaminate with one layer of nonwoven on the male side of the formed film (e.g., the side where the apertures terminate); and (ii) a trilaminate with one layer of nonwoven on each side of the formed film. For one set of samples the laminate was bonded by liberal application of Krylon® All Purpose 7010 spray adhesive on each side of the film followed by pressure to assure a complete bond. For the other set of samples, the samples were not laminated. The composite web samples were stretched on a MTS Synergie 200 tensile tester (MTS Systems Corporation, Eden Prairie, Minn.) at a rate of 200 mm/minute with a gauge length of 2 inches (50.8 millimeters). The results are shown in Table 1 below.

TABLE 1

Tensile Properties of Activated Laminate Webs

| | Sample | |
|---|---|---|
| | A | B |
| State of Laminate | Unbonded | Bonded |
| MD Tensile @ 200% | 23927 | 27158 |
| MD Elongation at Break | 439 | 257 |

The samples tested were bilaminates. The "unbonded" material was an elastic film and a separate nonwoven that were not previously bonded, but rather bonded when activated. The "bonded" material was a laminate of the same elastic film and nonwoven glue bonded together prior to entering the activation. The data in the table reveal that the unbonded laminated materials had superior elastic properties, when compared to the laminates that were bonded prior to activation.

The advantage of activating the webs together in an unbonded state is clearly seen in Table 1, in which the unbonded web is seen to have higher elongation to break values. The higher elongation values demonstrate that the unbonded materials can survive more aggressive activation than the bonded samples. In addition, the composite web that is activated in the unbonded state therefore appears softer to a user's hand than does the web that was activated in a bonded state.

While the disclosure and examples presented above have been limited to certain particularly preferred embodiments, it is recognized that similar advantages over the existing art will be obtained by other embodiments that will be evident to those skilled in the art, and that various changes and modifications can be made without departing from the spirit and scope of the embodiments. All such modifications are intended to be encompassed within the scope of the appended claims.

We claim:

1. A method for producing a composite web comprising:
   (i) supplying two or more webs together in face to face relationships into a means for stretching the webs, where the webs are in an unbonded state relative to each other;
   (ii) stretching the two or more webs together until breakage of inter fiber bonds occur while the webs are in face to face relationship and in an unbonded state to induce softness to produce activated and non bonded webs; and
   (iii) bonding the activated and non bonded webs together in a face to face relationship with a bonding means to form a composite web.

2. The method of claim 1, wherein the means for stretching comprises two or more rolls with intermeshing gears.

3. The method of claim 1, wherein the bonding means comprises a means selected from the group consisting of thermal bonding, adhesive bonding, point bonding, mechanical bonding, ultrasonic bonding, solvent bonding, and combinations thereof.

4. The method of claim 2 wherein bonding takes place in the nip between two of the intermeshing gear rolls.

5. The method of claim 2, wherein bonding takes place after the webs have been stretched, and wherein bonding takes place in the nip between a nip roll and one of the intermeshing gear rolls by applying a force against the teeth of the intermeshing gear roll by the nip roll through the webs, the force being sufficient to form bonds between the webs that are in contact with each other.

6. The method of claim 1, wherein one or more of the webs is a nonwoven web.

7. The method of claim 1, wherein one or more of the webs is a perforated film.

8. The method of claim 1, wherein one or more of the webs is an elastic film.

* * * * *